(12) United States Patent
Godfrin et al.

(10) Patent No.: US 10,286,008 B2
(45) Date of Patent: May 14, 2019

(54) METHOD FOR STABILISING SUSPENSIONS OF RED BLOOD CELLS ENCAPSULATING AN ACTIVE INGREDIENT

(71) Applicant: ERYTECH PHARMA, Lyons (FR)

(72) Inventors: Yann Godfrin, Lyons (FR); Vanessa Bourgeaux, Lyons (FR); Jérôme Bailly, Chassieu (FR)

(73) Assignee: ERYTECH PHARMA, Lyons (FR)

( * ) Notice: Subject to any disclaimer, the term of this patent is extended or adjusted under 35 U.S.C. 154(b) by 147 days.

(21) Appl. No.: 14/889,083

(22) PCT Filed: May 7, 2014

(86) PCT No.: PCT/EP2014/059327
§ 371 (c)(1),
(2) Date: Nov. 4, 2015

(87) PCT Pub. No.: WO2014/180897
PCT Pub. Date: Nov. 13, 2014

(65) Prior Publication Data
US 2016/0095884 A1    Apr. 7, 2016

(30) Foreign Application Priority Data
May 7, 2013 (FR) ...................................... 13 54204

(51) Int. Cl.
| A61K 9/00 | (2006.01) |
|---|---|
| A61K 9/50 | (2006.01) |
| A61K 35/18 | (2015.01) |
| A61K 35/12 | (2015.01) |

(52) U.S. Cl.
CPC ............ *A61K 35/18* (2013.01); *A61K 9/0019* (2013.01); *A61K 9/5068* (2013.01); *A61K 2035/124* (2013.01)

(58) Field of Classification Search
None
See application file for complete search history.

(56) References Cited

U.S. PATENT DOCUMENTS

| 4,321,259 | A | 3/1982 | Nicolau et al. |
|---|---|---|---|
| 4,327,710 | A | 5/1982 | DeLoach et al. |
| 4,389,209 | A | 6/1983 | DeLoach et al. |
| 4,478,824 | A | 1/1984 | Franco et al. |
| 4,652,449 | A | 3/1987 | Ropars et al. |
| 4,752,586 | A | 6/1988 | Ropars et al. |
| 4,801,777 | A | 1/1989 | Auerbach |
| 5,589,389 | A | 12/1996 | Pages et al. |
| 5,612,207 | A | 3/1997 | Nicolau et al. |
| 6,139,836 | A | 10/2000 | Magnani et al. |
| 6,610,702 | B2 | 8/2003 | Lehn et al. |
| 8,617,840 | B2 | 12/2013 | Godfrin |
| 8,852,880 | B2 | 10/2014 | Godfrin |
| 9,580,739 | B2 | 2/2017 | Godfrin |
| 2007/0135343 | A1 | 6/2007 | Webb et al. |
| 2008/0261262 | A1 | 10/2008 | Godfrin |
| 2011/0014171 | A1 | 1/2011 | Bourgeaux et al. |
| 2012/0121570 | A1 | 5/2012 | Godfrin |
| 2014/0010795 | A1 | 1/2014 | Bourgeaux et al. |
| 2014/0154797 | A1 | 6/2014 | Godfrin |
| 2014/0363413 | A1 | 12/2014 | Bourgeaux et al. |
| 2015/0071894 | A1 | 3/2015 | Godfrin |
| 2017/0021022 | A1 | 1/2017 | Webb et al. |

FOREIGN PATENT DOCUMENTS

| CN | 1149338 A | 5/1997 |
|---|---|---|
| CN | 101163497 A | 4/2008 |
| CN | 101965182 A | 2/2011 |
| JP | A-1993507070 | 10/1993 |

OTHER PUBLICATIONS

International Search Report dated Aug. 11, 2014 in PCT/EP2014/059327.
Morand, et al., "Transport of fatty acids across the membrane of human erythrocyte ghosts", 1985, pp. 68-76, vol. 835, Biochimica et Biophysica Acta.
Rossi, et al., "Macrophage depletion induced by clodronate-loaded erythrocytes", Feb. 2005, pp. 99-111, vol. 13, No. 2., Journal of Drug Targeting.
Millan, et al., "Factors associated with the performance of carrier erythrocytes obtained by hypotonic dialysis", Sep.-Oct. 2004, pp. 132-140, vol. 33, No. 2, Blood Cells Mol. Dis.
Schrijvers, et al, "Role of Red Blood Cells in Pharmacokinetics of Chemotherapeutic Agents", 2003, pp. 779-791, vol. 42, No. 9, Clin. Pharmacocokinet.
Hussain, et al., "Erythrocyte Osmotic Fragility in Man: Variation with Age and Sex", Aug. 1984, pp. 716-718, vol. 57, No. 4, BR. J. Haemateology.

(Continued)

*Primary Examiner* — Blaine Lankford
(74) *Attorney, Agent, or Firm* — B. Aaron Schulman, Esq.; Stites & Harbison, PLLC

(57) ABSTRACT

A method for obtaining a stabilized suspension of red blood cells encapsulating an active ingredient, from resealed RBCs incorporating the active ingredient, the method comprising the incubation of the resealed RBCs in an incubation solution at an osmolality of no less than 280 m Osmol/kg, for a time of 30 minutes or more, the incubation solution being a solution that does not contain an agent which is denaturating for the RBC membrane, the liquid medium is then removed from the incubated suspension and the RBCs obtained are placed in suspension in a solution allowing the injection of the suspension in a patient. The suspensions obtained are particularly characterized by an extracellular haemoglobin level maintained at 0.5 or lower, in particular 0.2 g/dl or lower and/or a hemolysis rate maintained at 2 or less, in particular 1% or less, at 72 h after placing in suspension in a preservation solution and at a temperature of between 2 and 8° C.

16 Claims, 1 Drawing Sheet

(56) References Cited

OTHER PUBLICATIONS

Davey, Richard J., M.D., "Transfusion-Associated Graft-Versus-Host Disease and the Irradiation of Blood Components", 1995, pp. 431-434, vol. 24, Nos. 1 & 2, Immunological Investigations.

Wang et al., "Evaluation of immunologic crossreaction of antiasparaginase antibodies in acute lymphoblastic leukemia (ALL) and lymphoma patients", Leukemia (2003) 17, 1583-1588.

Opposition filed Aug. 6, 2012 in corresponding European Application No. 05768180.1 (European Patent 1773452) and Response filed Mar. 22, 2013.

Ropars, et al., "Resealed Red Blood Cells as a New Blood Transfusion Product", 1985, pp. 82-91. No. 51, Biblthca haemat.

Kravtzoff, et al., "Improved Pharmacodynamics of L-asparaginase-loaded in human red blood cells", 1996, pp. 465-470, Eur. J. Clin. Pharmacol. 49.

Boucher Laurence et al: "Internalization and distribution of inositol hexakisphosphate in red blood cells", Biotechnology and Applied Biochemistry, vol. 24, No. 1, 1996, pp. 73-78.

Millan C G et al: "Drug enzyme and peptide delivery using erythrocytes as carriers", Journal of Controlled Release, Elsevier Science Publishers B.V. Amsterdam, NL, vol. 95, No. 1, Feb. 20, 2004 (Feb. 20, 2004), pp. 27-49.

Didelon J et al: "Validation of a test of the red cell membrane osmotic resistance", Clinical Hemorheology and Microcirculation, vol. 23, No. 1, 2000, pp. 31-42.

Kravtzoff R et al: "Erythrocytes as carriers for L-asparaginase Methodological and mouse in-vivo studies", The Journal of Pharmacy and Pharmacology Jul. 1990, vol. 42, No. 7, Jul. 1990 (Jul. 1990), pp. 473-476.

Philip Seeman. "Transient holes in the erythrocyte membrane during hypotonic hemolysis and stable holes in the membrane after lysis by saponin and lysolecithin", J. Cell. Biol. 1967, 32(1): 55-70.

Labrude, et al., "L'Hematie Vecteur D'Enzyme et de Medicament", 1985, pp. 181-187, vol. 36, No. 4, Lyon Pharmaceutique.

Sadahiro et al, "Pharmacokenetic of 5-Fluorouracil Following Hepatic Intra-arterial Infusion in a VX2 Hepatic Metastasis Model", 2003, pp. 377-381, vol. 33, No. 8, Jpn J Clin Oncol.

Hamidi et al, "Carrier Erythrocytes: An Overview", 2003, pp. 9-20, vol. 10, No. 9, Drug Delivery.

Bax et al, "Survival of human carrier erythrocytes in vivo", 1999, pp. 171-178, vol. 96, Clinical Science.

Hussain et al, "Erythrocyte Osmotic Fragility in Man: Variation with Age and Sex", 1984, pp. 716-718, vol. 54, No. 4, Br. J. Haematol.

Kolanjiappan et al, "Measurement of erythrocyte lipids, lipid peroxidation, antioxidants and osmotic fragility in cervical cancer patients", 2002, pp. 143-149, Clinica Chimic Acta 326.

Wang et al, "Evaluation of immunologic crossreaction of antiasparaginase antibodies in acute lymphoblastic leukemia (ALL) and lymphoma patients", 2003, pp. 1583-1588, vol. 17, Leukemia.

Schrijvers, Dirk, "Role of Red Blood Cells in Pharmacokinetics of Chemoterapeutic Agents", 2003, pp. 779-791, vol. 42, No. 9, Clin. Pharmacokinet.

Didelon et al, "Osmotic fragility of the erythrocyte membrane: characterization by modeling of the transmittance curve as a function of the NaCI concentration", 2000, pp. 409-416, Biorheology 37.

Zocchi et al, "Encapsulation of doxorubicin in liver-targeted erythrocytes increases the therapeutic index of the drug in a murine metastatic model", Mar. 1989, pp. 2040-2044, vol. 86, Proc. Natl. Acad. Sci., USA.

Bailleul et al, "Internalization of Various Allosteric Effectors of Hemoglobin in Human Erythrocytes", 1991, pp. 9-16, vol. 81, Advances in the Biosciences.

Deleuze et al, "Enhanced $O_2$ transportation during cardiopulmonary bypass in piglets by the use of inositol hexaphoshate loaded red blood cells", 1992, pp. 239-242, vol. 15, No. 4, The International Journal of Artificial Organs.

Ropars et al, "Engineered erythrocytes: influence of $P_{50}$ rightward shift and oxemia on oxygen transport to tissues", Jul. 1998, pp. 508-512, Medical & Biological Engineering & Computing.

Sanz et al. (1999) Life Sciences, vol. 65, No. 26, pp. 2781-2789.

Tonetti, et al. (1990) Biotechnology and Applies Biochemistry 12, 621-629.

Jordan, et al., "Band-3 crosslinking-induced targeting of mouse carrier erythrocytes", 1999, pp. 59-65, vol. 29, Biotechnol. Appl. Biochem.

Clinical Hematology Test.

Rossi, et al, "Macrophage depletion induced by clodronate-loaded erythrocytes", Feb. 1, 2005, pp. 99-111, vol. 13, No. 2, Journal of Drug Targeting, Harwood Academic Publishers GMBH, DE.

Millan, et al, "Factors associated with the performance of carrier erythrocytes obtained by hypotonic dialysis", Sep. 1, 2004, pp. 132-140, vol. 33, No. 2, Blood Cells, Molecules and Diseases.

Morando, et al, "Transport of fatty acids across the membrane of human erythrocyte ghosts", Jun. 14, 1985, pp. 68-76, vol. 835, No. 1, Biochimica et Biophysica Acta (BBA)—Lipids and Lipid Metabolism.

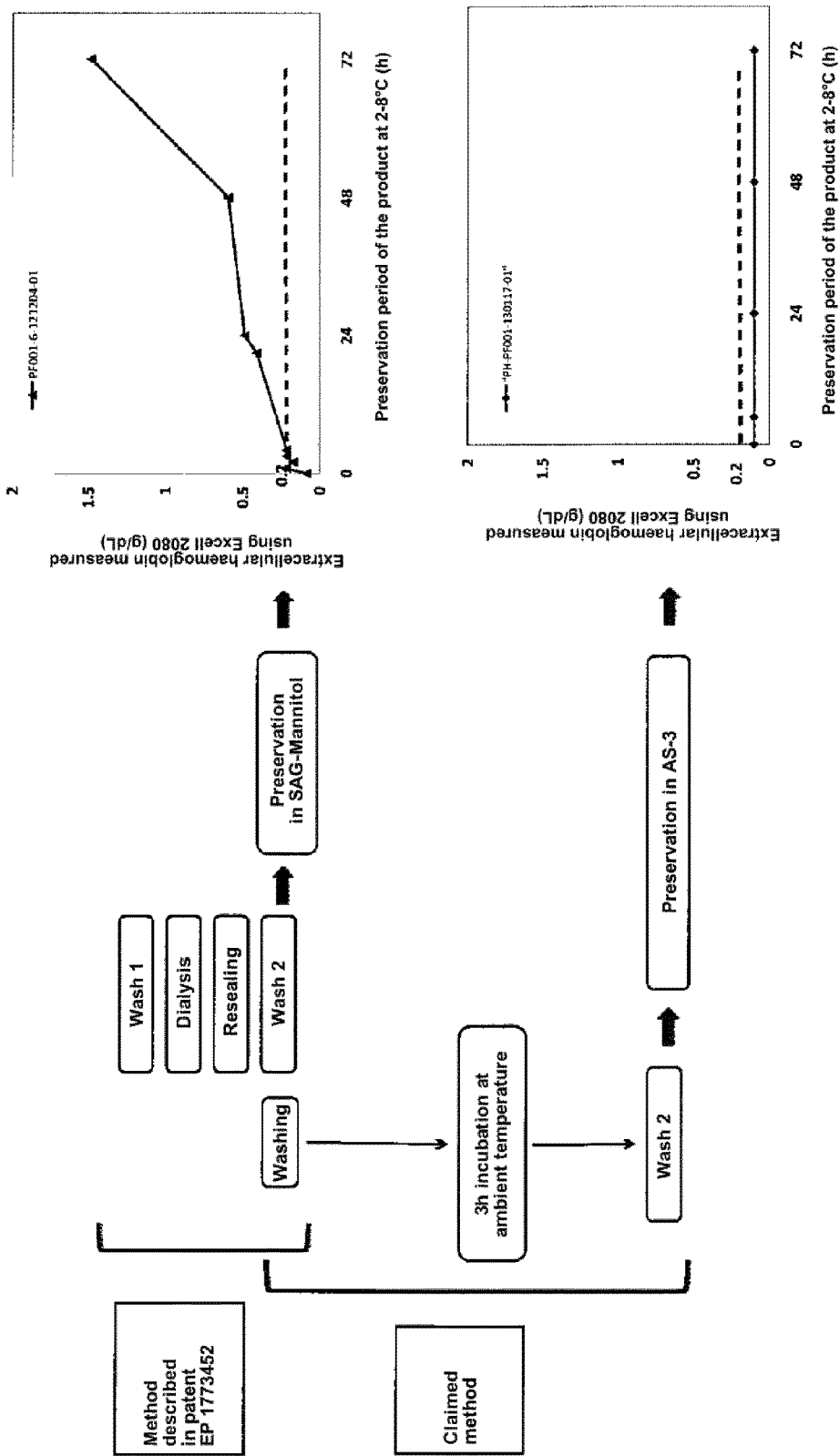

METHOD FOR STABILISING SUSPENSIONS OF RED BLOOD CELLS ENCAPSULATING AN ACTIVE INGREDIENT

The present invention concerns a method for stabilising suspensions of red blood cells encapsulating an active ingredient. The invention also concerns a method for preparing such suspensions, the treatment methods using these suspensions and novel stable suspensions of red blood cells encapsulating an active ingredient.

Various methods have been described to allow the incorporation of active ingredients into red blood cells. Among these methods, the so-called lysis-resealing technique is the most widespread. This technique comprises three variants which are hypotonic dialysis, hypotonic pre-swelling and hypotonic dilution, all based on the difference in osmotic pressure between the inside and outside of red blood cells. These variants have in common the five following steps: a blood cell residue is washed and centrifuged one or more times in physiological buffer, the red blood cells are placed in contact with a hypotonic liquid medium leading to the opening of pores in the erythrocyte membrane, the active ingredient enters the red blood cells, the pores are closed (resealed) using a hypertonic buffer thereby enclosing the active ingredient inside the red blood cells which are then placed in suspension in a preservation solution. The hypotonic dialysis method is the most advantageous and is the subject of industrial development. The method described in EP 1 773 452 is the method currently offering the best performance and has the advantage of being reproducible and of improving the encapsulation yield of active ingredient.

The stability of the products thus obtained is a key element for use thereof in human therapy. In particular, the quantity of extracellular haemoglobin contained in the product at the time it is injected into the patient must be lower than a predetermined threshold. For example, the threshold required by the American Food and Drug Administration FDA for extracellular haemoglobin is 0.2 g/dL or less in the end product used for human injection.

The products obtained with prior art methods undergo haemolysis during their storage period and transport before injection. This haemolysis, due to bursting of the most fragile red blood cells, releases haemoglobin into the extracellular medium with the result that these products no longer meet FDA requirements at the time they are injected.

It is therefore an objective of the invention to propose a method with which it is possible to improve the stability of red blood cell suspensions encapsulating an active ingredient One objective in particular of the invention is to propose a method allowing suspensions of red blood cells to be produced which incorporate an active ingredient and have a stable extracellular haemoglobin level after storage, or which remain in conformity with the recommendations given by the FDA or any other health authority.

It is another objective of the invention to propose a said method applicable to any suspension of red blood cells encapsulating an active ingredient, irrespective of the method used for preparation thereof, in particular using a lysis-resealing method.

A further objective of the invention is to propose a said method allowing the production of a suspension of red blood cells encapsulating an active ingredient that is stabilised and has a high cell yield.

These objectives, and others, can be reached by eliminating the most fragile red blood cells from the suspension resulting from the encapsulation process, i.e. post-resealing, so as to obtain a suspension comprising haemolysis-resistant red blood cells in the largest possible proportion. The suspension of red blood cells can therefore be preserved up until the time it is injected into a patient without the suspension undergoing significant haemolysis, making it possible to have available a suspension at the time of injection that has a low level of extracellular haemoglobin. The method of the invention therefore provides for the elimination of the most fragile red blood cells, of extracellular haemoglobin and of extracellular active ingredient. The applicant has succeeded in achieving this whilst maintaining a good cell yield, finding a good compromise between the elimination of the most fragile and the retaining of the maximum number of red blood cells. The applicant has even been able to determine the conditions which surprisingly allow the stabilisation of a suspension of red blood cells encapsulating an active ingredient, whilst improving cell yield. By «encapsulating» is meant that the active ingredient is essentially or fully contained on the inside. «Essentially» means that a minority proportion of active ingredient may nevertheless be trapped in the membrane.

By «encapsulating an active ingredient» is meant that the red blood cells incorporate a molecule having an active ingredient function, or that the assembly formed by the red blood cell and the molecule it incorporates has an active ingredient function.

By «incubation solution» is meant the solution in which the red blood cells encapsulating an active ingredient are contained during the incubation step. Incubation can be conducted over a broad haematocrit range, in particular between 10 and 85 haematocrit.

By «preservation solution» is meant the solution in which the stabilised red blood cells encapsulating an active ingredient are placed in suspension in their form suitable for storage until use. A preservation solution preferably comprises at least one agent promoting the preservation of red blood cells, chosen in particular from among glucose, dextrose, adenine and mannitol.

By «fragile red blood cells» is meant the red blood cells, derived from the incorporation procedure, which are likely to lyse once in suspension in a preservation solution when the suspension is stored at between 2 and 8° C., in particular after 1 to 72 h.

By «initial haematocrit» is meant the haematocrit before cell loss due to lysis of the fragile red blood cells during incubation.

The notion of «stabilisation» is assessed essentially by the stability over time of the red blood cells incorporating an active ingredient, particularly in terms of loss of intracellular haemoglobin or extracellular haemoglobin level.

By «stabilised suspension of red blood cells» is notably meant a suspension having an extracellular haemoglobin level remaining at 0.5 g/dL or lower, in particular 0.3 g/dL or lower, preferably 0.2 g/dL or lower up until its use in man, such use possibly occurring from 1 to 72 hours after the production of the batch of red blood cells incorporating the active ingredient. It may also be characterized by a haemolysis rate that is maintained at 2 or lower, in particular 1.5 or lower, preferably 1% or lower at 72 h and storage at a temperature between 2 and 8° C.

By «ready-to-use stabilised suspension of red-blood cells» is meant the stabilised suspension in a solution allowing injection into a patient, particularly in preservation solution. Its haematocrit is generally 40% or higher.

By «residue of red blood cells» or packed red blood cells is meant a concentrate of red blood cells collected after separation of the red blood cells from the liquid medium in which they were previously in suspension. Separation can be performed by filtration or centrifugation. Centrifugation is the means generally used for such separation. A residue comprises a certain proportion of liquid medium. In general, the haematocrit of the residue is between 70 and 85%.

The method can be applied irrespective of the technique used to incorporate or encapsulate the active ingredient. It can be most particularly applied to the leading lysis-resealing technique, in particular using hypotonic dialysis, preferably the method described in EP 1 773 452 to which persons skilled in the art may refer. The content of EP 1 773 452 is incorporated herein by reference. As it will be understood by reading the following description, the stabilisation method of the invention may be applied to a suspension or to a residue of resealed red blood cells encapsulating the active ingredient, or may include the lysis and resealing steps performed until a suspension or a residue of resealed red blood cells is obtained.

The present invention has thus as an object a method for obtaining a stabilised suspension of red blood cells (RBCs) encapsulating an active ingredient, from resealed erythrocytes incorporating the active ingredient. The process comprises the incubation of the resealed red blood cells in an incubation solution at an osmolality of no less than 280 mOsmol/kg, in particular between about 280 and about 380 mOsmol/kg, preferably between about 290 and about 330 mOsmol/kg. Incubation is particularly conducted for a time of 30 minutes or more, in particular for a time of 1 h or more. Incubation is called post-resealing, i.e. it is performed on resealed RBCs. The liquid medium is then removed from the incubated suspension and the RBCs obtained are placed in suspension in a solution allowing the injection of the suspension in a patient, preferably a preservation solution allowing the injection of the suspension in a patient.

The incubation solution is typically a saline solution, comprising at least ions allowing to adjust osmolality (for example, a solution based on NaCl, KCl and/or phosphate). It may comprise further ingredients, in particular carbon hydrates, especially sugars, and/or acidic and/or basic additives allowing the adjustment of the pH (in particular between about 6 and about 8.5, preferably between about 7 and about 7.5). The incubation solution does not comprise any agent that is denaturating for the RBC membrane, such as bridging or cross-linking chemical agents such as Bis (Sulfosuccinimidyl) suberate (BS3), glutaraldehyde and neuraminidase. It is thus an inert incubation solution or a solution that does not fragilise the membrane of the resealed RBCs.

In an embodiment, the method comprises, before incubation, encapsulating by lysis-resealing the active ingredient into RBCs and obtaining resealed RBCs comprising the active ingredient.

Preferably, a washing (at least 1 washing cycle) of the resealed RBCs is made before incubation.

Resealed RBCs to which the method is applied may be a suspension of RBCs in a preservation solution. It is then possible to dilute the preservation solution with incubation solution in order to get the osmolality at a value in accordance with the invention. Alternatively, the RBCs may be separated from the preservation solution, for example by centrifugation or filtration, then the incubation solution is added. It is also possible to wash the resealed RBCs (at least 1 cycle, as described hereafter); the washing cycle preferably comprises dilution of the suspension, then separation, before placing in suspension in the incubating solution. Resealed RBCs to which the method is applied may also be a suspension of resealed RBCs that are still in the resealing solution. It is then possible to separate the RBCs from the resealing solution, for example by centrifugation or filtration, and/or to wash the resealed RBCs (at least 1 cycle, as described hereafter); the washing cycle preferably comprises dilution of the suspension, then separation, before placing in suspension in the incubating solution.

The method thus comprises placing and incubating the resealed RBCs in an incubation solution at an osmolality of no less than 280 mOsmol/kg, in particular between about 280 and about 380 mOsmol/kg, preferably between about 290 and about 330 mOsmol/kg.

The subject of the present invention is in particular a method for obtaining a stabilised suspension of red blood cells (RBCs) encapsulating an active ingredient, comprising the encapsulation of an active ingredient inside RBCs via lysis-resealing, the obtaining of a suspension or residue containing resealed RBCs incorporating the active ingredient, the washing (at least 1 washing cycle) of the resealed RBCs, then their placing and incubation in an incubation solution at an osmolality of no less than 280 mOsmol/kg, in particular between about 280 and about 380 mOsmol/kg, preferably between about 290 and about 330 mOsmol/kg. Incubation is particularly conducted for a time of 30 minutes or more, in particular for a time of 1 h or more. The liquid medium is then removed from the incubated suspension and the RBCs obtained are placed in suspension in a solution allowing the injection of the suspension in a patient, preferably a preservation solution allowing the injection of the suspension in a patient. The indicated osmolality is that of the solution in which the RBCs are in suspension or in a residue at the time under consideration.

The method conforming to the invention particularly comprises the following steps:

(a) encapsulating an active ingredient inside RBCs, comprising the contacting with a hypotonic medium (allowing opening of pores in the membrane of the RBCs), contacting with the active ingredient (to allow entry into the RBCs), resealing the RBCs in particular using an isotonic or hypertonic medium, advantageously hypertonic;

(b) obtaining or preparing a suspension or residue containing RBCs incorporating the active ingredient and a solution at an osmolality of no less than 280 mOsmol/kg, in particular between about 280 and about 380 mOsmol/kg, preferably between about 290 and about 330 mOsmol/kg;

(c) incubating the residue or suspension of step (b) as such or after the addition of an incubation solution, at an osmolality of no less than 280 mOsmol/kg, in particular between about 280 and about 380 mOsmol/kg, preferably between about 290 and about 330 mOsmol/kg, for a time of 30 minutes or longer, in particular 1 h or longer;

(d) eliminating the liquid medium from the suspension incubated at step (c), (e) placing the RBCs obtained at (d) in suspension in a solution allowing injection of the suspension in a patient, preferably a preservation solution allowing injection of the suspension in a patient.

According to a first modality, the step following after encapsulation by lysis-resealing, in particular step (b), comprises at least 1 washing cycle, preferably 2 or 3 washing cycles, by dilution of the suspension of residue comprising resealed RBCs, e.g. obtained after the lysis-resealing step or step (a) in a solution at an osmolality of no less than 280 mOsmol/kg, in particular between about 280 and about 380 mOsmol/kg, preferably between about 290 and about 330 mOsmol/kg, then obtaining a residue of RBCs or a suspension. This residue or this suspension contains RBCs incorporating the active ingredient and a solution at an osmolality of no less than 280 mOsmol/kg, in particular between about 280 and about 380 mOsmol/kg, preferably between about 290 and about 330 mOsmol/kg. The following steps, e.g. (c), (d) and (e) are then applied.

The steps following after lysis-resealing e.g. (b) to (e), are conducted under conditions leading to lysis of the fragile red blood cells or a majority thereof, in particular more than 50, 60, 70, 80 or 90%, or more. For this purpose it can be acted upon incubation time, incubation temperature and the osmolality of the solution in which the RBCs are in suspension. The higher the osmolality, the longer the incubation time. The lower the osmolality, the shorter the incubation time to obtain the same effect. Similarly, the higher the temperature, the shorter the incubation time and conversely. One or more washing cycles will then allow elimination of cell debris and extracellular haemoglobin, and of extracellular active ingredient.

According to the invention, a washing cycle comprises the dilution of the suspension or residue of RBCs, then the separation of the RBCs and washing solution. Preferably, a washing step preferably comprises 2 or 3 dilution-separation cycles. Separation can be performed using any suitable means such as filtration and centrifugation. Centrifugation is preferred. Washing with the incubation solution is preferred. Incubation is not limited by the haematocrit of the suspension. It is therefore possible to incubate a suspension having an initial haematocrit generally of between 10 and 85%, in particular between 40 and 80%. The term residue is rather more used on and after 70%, and suspension below this value.

The elimination step or step (d) is intended to «eliminate» the liquid part from the incubated suspension or residue in particular to remove cell debris and extracellular haemoglobin, and consequently extracellular active ingredient.

According to a first modality of the elimination step or step (d), a separation in particular centrifugation is performed, this being particularly applicable to a suspension. This separation can be followed be one or more e.g. 2 or 3 washing cycles by dilution in isotonic solution, followed by separation in particular by centrifugation.

According to a second modality of the elimination step or step (d), a dilution is performed before separation in particular by centrifugation, this being applicable to a suspension or a residue. Dilution can be performed in particular with an isotonic washing solution or preservation solution.

At the final step or step (e) the final suspension is prepared such that it can be administered to a patient, without any other treatment.

According to a first modality of this step, the residue of RBCs derived from the elimination step or step (d) is diluted with the injection solution, in particular preservation solution.

According to a second modality of this step, one or more washing cycles are performed on the residue of RBCs derived from the elimination step or step (d) with the injection, particularly preservation solution, by dilution followed by separation. After washing, the RBCs are replaced in suspension in the injection, in particular preservation, solution.

The method of the invention may further comprise one, several or all the following characteristics:
the incubation step or step (c) is conducted at a temperature of between about 2 and about 39° C., for sufficient time to ensure lysis of the fragile RBCs;
the incubation step or step (c) is conducted at low temperature, particularly between about 2 and about 10° C., in particular between about 2 and about 8° C., and lasts about 1 h to about 72 h, in particular from about 6 h to about 48 h, preferably from about 19 h to about 30 h;
the incubation step or step (c) is conducted at a higher temperature between about 20 and about 39° C., in particular at ambient temperature (25° C.±5° C.) and lasts about 30 min to about 10 h, particularly from about 1 h to about 6 h, preferably from about 2 h to about 4 h; it is possible to work at a temperature even higher than ambient temperature but this may have a negative impact on cell yield, P50 and/or 2,3-DPG content;
at the incubation step or step (c), the suspension has an initial haematocrit of between 10 and 85%, particularly between 40 and 80%; it is possible to incubate a residue derived from separation having a haematocrit of between 70 and about 85% for example, or a diluted residue having a haematocrit of between about 40 and 70%;
the incubation step comprises agitation of the suspension;
the incubation step does not comprise any agitation;
as solution for washing and/or incubation, an aqueous NaCl solution is used at a concentration to obtain the desired osmolality; for example a solution may comprise 0.9% NaCl; notably in addition to NaCl or another salt source (e.g. KCl, phosphate), this solution may also contain glucose in particular glucose monohydrate, monosodium phosphate dihydrate, disodium phosphate dodecahydrate; for example a composition comprises: 0.9% NaCl, 0.2% glucose monohydrate, 0.034% monosodium phosphate dihydrate, 0.2% disodium phosphate dodecahydrate;
the washing at the final step or step (e) is performed with the preservation solution;
the osmolality of the solution (liquid part) in the ready-to-use suspension or suspension to be injected in the patient is between about 280 and about 380 mOsmol/kg, preferably between about 290 and about 330 mOsmol/kg;
the haematocrit of the ready-to-use suspension or suspension able to be injected in the patient is 40% or higher;
all the washing, incubation steps are conducted with the preservation solution;
the washing solution of step (b) and/or the washing solution of step (e) and the preservation solution are of same composition and comprise one or more compounds promoting preservation of the red blood cells;
the preservation solution (and when applicable the washing or incubation solutions) is an aqueous solution containing NaCl, adenine and at least one compound from among glucose, dextrose and mannitol;
the preservation solution (and when applicable the washing or incubation solutions) contain NaCl, adenine and dextrose, preferably AS3 medium;
the preservation solution (and when applicable the washing or incubation solutions) contain NaCl, adenine, glucose and mannitol, preferably SAG-Mannitol or ADsol medium.

The present invention can also be defined by a method for obtaining a stabilised suspension of RBCs incorporating an active ingredient, particularly comprising the following steps:
(a) encapsulating an active ingredient inside RBCs, comprising the contacting with a hypotonic medium (allowing the opening of pores in the membrane of the RBCs), contacting with the active ingredient (to allow entry thereof into the RBCs), resealing the RBCs with an isotonic or hypertonic medium and harvesting a suspension or residue of RBCs containing a group of so-called fragile RBCs namely which, once in suspension in a preservation solution, are likely to be lysed when the suspension is stored at between 2 and 8° C., particularly after 1 to 72 h, (b-c) washing and incubating the RBCs obtained at (a) in a solution and under conditions leading to lysis of fragile RBCs, or a majority thereof, in particular more than 50, 60, 70, 80 or 90%, (d) eliminating the liquid medium from the suspension incubated at the preceding step, (e) suspending the RBCs obtained at (d) in a solution allowing injection of the suspension in a patient, preferably a preservation solution allowing injection of the suspension in a patient.

According to a characteristic, step (b) comprises the obtaining or preparation of a suspension or residue comprising RBCs incorporating the active ingredient and a solution at an osmolality of no less than 280 mOsmol/kg, in particular between about 280 and about 380 mOsmol/kg, preferably between about 290 and about 330 mOsmol/kg.

According to a characteristic, step (c) comprises the incubation of the residue or suspension of step (b) as such or after addition of an incubation solution at an osmolality of no less than 280 mOsmol/kg, particular between about 280 and about 380 mOsmol/kg, preferably between about 290 and about 330 mOsmol/kg, for a time of 30 minutes or more, in particular 1 h or more.

According to a characteristic, step (d) comprises the washing of the RBCs obtained at (c) to eliminate cell debris and extracellular haemoglobin, in particular 2 or 3 washing cycles.

This method may reproduce the two embodiments and their various modalities and characteristics described herein.

The methods of the invention particularly comprise the following step:

(a) encapsulating an active ingredient inside RBCs, comprising the contacting with a hypotonic medium to open pores in the membrane of the RBCs, contacting with the active ingredient to allow entry thereof into the RBCs, resealing of the RBCs using an isotonic or hypertonic medium. It is to be noted that the active ingredient may be present in the suspension of RBCs before lysis thereof, or it may be added during lysis or after lysis, but always before resealing.

In one embodiment of this step (a), the method comprises the following sub-steps:

(a1) providing a suspension of red blood cells at a haematocrit of no less than 60 or 65%, (a2) measuring the osmotic fragility of the RBCs in this suspension, (a3) procedure for lysis and internalisation of the active ingredient, comprising the flowing of the suspension of RBCs in a dialysis device, in particular a dialysis tube, in counter-flow to a lysis solution, adjusting the flow rate of the suspension of RBCs or adjusting the flow rate of the lysis solution, or adjusting the osmolarity of the lysis solution, as a function of the osmotic fragility measured at (a2), (a4) procedure for resealing of the RBCs.

In this embodiment, step (a1) comprises the washing/centrifuging of a cell residue, and the suspending of the washed RBCs in a physiological buffer at a haematocrit of no less than 60 or 65%.

Preferably a temperature of 2 to 8° C. is maintained throughout steps (a1) and (a3) and preferably the temperature of the products used is between 2 and 8° C.

Preferably, the resealing process of the RBCs is performed using a hypertonic solution and preferably at a temperature of between 30 and 40° C., in particular about 37° C.

After resealing, the RBCs are separated from the resealing medium using a separation procedure, preferably centrifugation. After centrifugation, a residue of RBCs is collected in the centrifuging tube or container. According to an advantageous characteristic of the invention, the collection is made of all or substantially all the fraction likely to contain RBCs, to increase the final cell yield after subsequent elimination of fragile cells.

In one embodiment the active ingredient is L-asparaginase. Other embodiments comprise the incorporation, preferably encapsulation of an active ingredient chosen from among: IHP, ADI, Factor VIII, Factor IX, alglucosidase, beta glucosidase, bisphosphonates, notably $2^{nd}$ and $3^{rd}$ generation, uricase, thymidine phosphorylase, adenosine deaminase, etc.

The RBCs, between steps (a) and (b) or after step (c) or (d), may undergo additional treatment to modify the surface of the RBCs or impart functionalities thereto by surface grafting or coupling to modify the properties thereof. According to a particular modality, this treatment is made post-incubation, especially after incubation step or after the washing which follows incubation. The treatment may be one of the following:

chemical treatment using agents modifying the surface of the RBCs, in particular bridging or cross-linking agents such as Bis(Sulfosuccinimidyl) suberate (BS3), glutaraldehyde and neuraminidase (denaturating agents);

heat treatment conducted for example under the following conditions: heating the RBCs for about 15 minutes to about 90 minutes, preferably from about 25 to about 50 minutes, at a temperature between about 42 and about 55° C., preferably between about de 47 and about 51° C.;

forming an immune complex with an antibody preferably of IgG sub-type; for example anti-Rhesus antibody, anti-glycophorine A antibody and anti-CR1 antibody (CR1=type-1 complement receptor).

Another subject of the invention is the use of an incubation step of a suspension of RBCs, which in particular encapsulate an active ingredient, followed by elimination of the incubation medium preferably by washing to remove the incubation medium so as to stabilise the RBCs or suspension of RBCs. Preferably this use further comprises the additional step of placing the RBCs in suspension in a preservation solution. The various more precise characteristics mentioned above apply to this subject of the invention.

In particular according to a characteristic, this incubation step comprises the incubation of a suspension or residue containing resealed RBCs incorporating the active ingredient and a solution at an osmolality of no less than 280 mOsmol/kg, in particular between about 280 and about 380 mOsmol/kg, preferably between about 290 and about 330 mOsmol/kg for a time of 30 minutes or more, in particular 1 h or more.

Further particularly, according to the invention, this incubation may comprise one or more of the following characteristics:

the incubation step is conducted at a temperature of between about 2 and about 39° C., for sufficient time to ensure the lysis of fragile RBCs;

the incubation step is conducted at low temperature, in particular between about 2 and about 10° C., more particularly between about 2 and about 8° C., and lasts for a time of about 1 h to about 72 h, in particular about 6 h to about 48 h, preferably from about 19 h to about 30 h;

the incubation step is conducted at a higher temperature of between about 20 and about 39° C., in particular at ambient temperature (25° C.±5° C.) and lasts about 30 min to about 10 h, in particular from about 1 h to about 6 h, preferably from about 2 h to about 4 h; it is possible to work at even higher temperature than ambient temperature but this may have a negative impact on cell yield, P50 and/or 2,3-DPG content;

at the incubation step, the suspension has an initial haematocrit of between 10 and 85%, in particular between 40 and 80%; it is possible to incubate a residue resulting from separation having a haematocrit of between 70 and about 85% for example, or a diluted residue having a haematocrit between about 40 and 70%;

the incubation step comprises agitation of the suspension;

the incubation step does not comprise any agitation.

A further subject of the invention is a stabilised suspension of RBCs encapsulating an active ingredient, able to be obtained by implementing the method of the invention.

In particular the suspension, in preservation solution, is characterized by an extracellular haemoglobin level which remains at 0.5 or lower, in particular 0.3 or lower, more particularly 0.2 or lower, preferably 0.15 or lower, further preferably 0.1 g/dl or lower at 72 h and storage at a temperature between 2 and 8° C.

In particular the suspension in preservation solution is characterized by an extracellular haemoglobin level which remains at 0.5 or lower, in particular 0.3 or lower, more particularly 0.2 or lower, preferably 0.15 or lower, further preferably 0.1 g/dl or lower for a time of between 24 h and 20 days, in particular between 24 and 72 h and storage at a temperature of between 2 and 8° C.

The extracellular haemoglobin level is advantageously measured using the reference manual method described by G. B. Blakney and A. J. Dinwoodie, in Clin. Biochem. 8, 96-102, 1975. Automated equipment also exists allowing this measurement each at its own particular sensitivity. It was nevertheless shown in the examples using three different methods that with the method of the invention it is possible to obtain a conforming level or that the three methods can be used for this control.

In particular, the suspension in preservation solution is characterized by a haemolysis rate that is maintained at 2 or lower, in particular 1.5 or lower, preferably 1% or lower at 72 h and storage at a temperature between 2 and 8° C.

In particular, the suspension in preservation solution is characterized by a haemolysis rate maintained at 2 or lower, in particular 1.5 or lower, preferably 1% or lower for a time between 24 h and 20 days, in particular between 24 and 72 h and at a temperature between 2 and 8° C.

In particular, the haematocrit of the suspension is no 40% or higher.

In one embodiment, the active ingredient is L-asparaginase. Other embodiments comprise the incorporation preferably encapsulation of an active ingredient chosen from among: IHP, ADI, Factor VIII, Factor IX, alglucosidase, beta-glucosidase, bisphosphonates, particularly $2^{nd}$ and $3^{rd}$ generation, uricase, thymidine phosphorylase, adenosine deaminase, etc.

Advantageously, the suspension in preservation solution is ready to use whilst having a low extracellular haemoglobin level, conforming in particular to FDA recommendations.

A further subject of the invention is a therapeutic treatment method by injection of a suspension of RBCs encapsulating an active ingredient.

In a first embodiment of this method, the injection is given to a patient of a suspension of RBCs encapsulating an active ingredient prepared between 1 and 72 h, in particular between 10 and 72 h before injection. The haematocrit of this suspension is 40% or higher. It is contained in a preservation solution. The extracellular haemoglobin level is 0.5 or lower, in particular 0.3 or lower, more particularly 0.2 or lower, preferably 0.15 or lower, further preferably 0.1 g/dl or lower, and/or the haemolysis rate is 2 or lower, in particular 1.5 or lower, preferably 1% or lower. The suspension is not subjected to washing or similar before injection.

In another embodiment, this method comprises the steps of providing a cell residue, placing it in suspension in physiological buffer at a haematocrit of 60 or 65% or higher, encapsulating an active ingredient in these RBCs using lysis and resealing procedure, incubating the RBCs obtained, washing the latter and collecting a final suspension of RBCs. The haematocrit of the suspension is 40% or higher. It is contained in a preservation solution. This suspension is stored at a temperature between 2 and 8° C. This final suspension is injected in the patient between 1 h and 72 h preferably between 24 and 72 h after preparation of the suspension. The extracellular haemoglobin level of this suspension is 0.5 or lower, in particular 0.3 or lower, more particularly 0.2 or lower, preferably 0.15 or lower, further preferably 0.1 g/dl or lower and/or its haemolysis rate is 2 or lower, in particular 1.5, or lower preferably 1% or lower. The suspension is not subjected to washing or similar before injection.

This method particularly comprises the following steps:
(a1) providing a suspension of RBCs at a haematocrit of 60 or 65% or higher,
(a2) measuring the osmotic fragility of the RBCs in this suspension,
(a3) lysis and active ingredient internalisation procedure comprising the flowing of the suspension of RBCs in a dialysis tube, in counter-flow to a lysis solution, adjusting the flow rate of the suspension of RBCs or adjusting the flow rate of the lysis solution, or adjusting the osmolarity of the lysis solution, as a function of the osmotic fragility measured at (a2),
(a4) resealing procedure of the RBCs,
(b) optionally at least one washing cycle by dilution of the suspension or residue obtained at (a4) in a solution, the collection of a residue of RBCs or suspension in the washing solution,
(c) incubating the residue or suspension of step (a4) or (b) as such or after addition of an incubation solution,
(d) eliminating the liquid medium from the suspension incubated at step (c),
(e) placing the RBCs obtained at (d) in suspension in a solution allowing injection in a patient, in particular a preservation solution.

In one embodiment of this method, the RBCs enclose L-asparaginase. The active ingredient may also be one of the other active ingredients mentioned above, but is not limited thereto.

The invention will now be described in more detail with the help of embodiments taken as non-limiting examples with reference to the drawing in which the single FIGURE schematises the method described in EP 1 773 452 and the method of the invention, and gives the results obtained for each thereof in terms of extracellular haemoglobin over a period of 72 hours.

EXAMPLE 1

Incubation of Red Blood Cells in NaCl+Glucose at Ambient Temperature Over a Variable Period Residues of human RBCs were treated in the absence or presence of active ingredient (L-asparaginase) following the method described in patent EP 1 773 452 up until completion of resealing, and suspensions of RBCs were collected in blood pouches. The pouches of RBCs were transferred to a washer (Cobe 2991). The suspensions were pre-diluted with 0.9% NaCl and 0.2% glucose, then transferred to centrifugation pouches. The suspensions were centrifuged at 3000 rpm for 2 min. The supernatants were then directed towards the waste pouch at a supernatant outflow rate set at 350 ml/min. The dilution/centrifugation operation was repeated two more times to terminate the washing cycle. The centrifugation pouches containing RBCs at 80% haematocrit were left at ambient temperature (24±5° C.) in the washer for 30 min, 1 h or 3 h. After incubation, another washing cycle was performed. The RBCs were then replaced in suspension with 100 ml of AS-3 (Caridian BCT) preservation solution and stored at 5±3° C. The stability of the product was determined by measuring extracellular haemoglobin on the day of manufacture (D0), then 24 h later (D1), and 48 h later (D2), etc. This measurement was performed using two methods: with an automated analyser (Cell Dyn Ruby: measurement at 555 nm, haemoglobin linearity 0.0-25.0 g/dl±0.3, coefficient of variation <2.0%–use of background noise function to measure traces of haemoglobin, sensitivity improved to ±0.2 g/dl; or Excell 2280 automated analyser: measurement at 540 nm, haemoglobin linearity 1.5-30.0 g/dl±0.1, coefficient of variation 1%), or by visible spectrophotometry at 577 nm following the reference manual method described by G. B. Blakney and A. J. Dinwoodie, in Clin. Biochem. 8, 96-102, 1975, incorporated herein by reference. In the examples the automated analysers were used following the manufacturer's recommendations. The results are given below.

1.1 Measurement of extracellular haemoglobin (en g/dl) performed using the Ruby analyser on 4 suspensions of RBCs encapsulating L-asparaginase:

|  | Batch N° | D0 | D1 | D2 | D3 |
|---|---|---|---|---|---|
| Incubation 3 h at ambient temperature | PH-PF001-130115-01 | 0.000 | 0.000 | 0.007 | 0.007 |
| | PH-PF001-130115-02 | 0.015 | 0.022 | 0.022 | 0.007 |
| | PH-PF001-130116-01 | 0.030 | 0.030 | 0.040 | 0.030 |
| | PH-PF001-130116-02 | 0.000 | 0.007 | 0.007 | 0.013 |
| | PH-PF001-130117-01 | 0.007 | 0.020 | 0.010 | 0.030 |

1.2 Measurement of extracellular haemoglobin (in g/dl) by spectrophotometry on 3 suspensions of RBCs encapsulating (ERY-ASP-121217-CG) or not encapsulating (ERY-121210-MA and ERY-121217-QB) L-asparaginase:

|  | Batch No | D0 | D1 | D2 | D3 | D8 |
|---|---|---|---|---|---|---|
| Incubation 3 h at ambient temperature | ERY-121210-MA | 0.120 | 0.120 | 0.127 | 0.141 | 0.188 |
| | ERY-121217-QB | 0.123 | 0.146 | 0.139 | 0.152 | — |
| | ERY-ASP-121217-CG | 0.084 | 0.077 | 0.081 | 0.098 | — |

1.3 Measurement of extracellular haemoglobin (in g/dl) using the Excel 2280 analyser on 2 suspensions of RBCs; the first encapsulating L-asparaginase, the second with no active ingredient:

|  | Batch No | D0 | D1 | D2 | D3 | D4 |
|---|---|---|---|---|---|---|
| 1 h at ambient temperature | ERY-ASP-130228-EC | 0.11 | — | — | — | 0.18 |
| 30 min at ambient temperature | GR-LR-130325-QB | 0.12 | 0.11 | 0.12 | 0.12 | 0.12 |

This method comprising an incubation step of RBCs in NaCl+glucose (time varying between 30 min and 3 h) allowed a stable product to be obtained with extracellular haemoglobin levels lower than 0.2 g/dl at D3 (72 h) and even for longer up to D8 i.e. 8 days after manufacture of the product. These results were confirmed by measurement of extracellular haemoglobin performed using 3 different methods.

EXAMPLE 2

Changes in Extracellular Haemoglobin Levels During Incubation at Ambient Temperature A residue of human RBCs was treated as in Example 1, not containing any active ingredient. During incubation at ambient temperature aliquots were taken, centrifuged at 1000 g for 10 min at 4° C. The supernatants were colected, and the haemoglobin level determined by visible spectrophotometry at 577 nm. The results are given below:

| | Incubation time at ambient temperature in h | | | | |
|---|---|---|---|---|---|
| | 0 | 0.5 | 1 | 2 | 3 |
| Haemoglobin in supernatant (g/dl) | 1.418 | 1.848 | 2.063 | 2.793 | 3.089 |

The results show that haemolysis of the RBCs was constant during the 3 h incubation time in NaCl+glucose at ambient temperature. This incubation step therefore makes a significant contribution towards eliminating the most fragile RBCs and hence it is indispensable for the method in order to obtain a stable end product. The incubation time can nevertheless be reduced to 30 min as shown in Example 1. The fragile, non-haemolysed RBCs during the incubation step are nonetheless weakened during this step and burst during the final wash.

EXAMPLE 3

Incubation of RBCs in Preservation Solution (AS-3 or SAG-mannitol) at 5±3° C. for 24 h Residues of RBCs were treated following the method described in patent EP 1 773 452 until completion of resealing, and incorporated L-asparaginase. The pouches of RBCs were transferred to a washer (Cobe 2991). The suspensions were pre-diluted with 0.9% NaCl and 0.2% glucose, then transferred to centrifugation pouches. The suspensions were centrifuged at 3000 rpm for 2 min. The supernatants were then directed towards the waste pouch at a supernatant outflow rate of 350 ml/min. The dilution/centrifugation operation was repeated two more times to terminate the washing cycle. The suspensions of RBCs at 80% haematocrit were then replaced in suspension with 100 ml of AS-3 or 80 ml of SAG-Mannitol preservation solution. The pouches of RBCs at ~50% haematocrit were then stored 24 h at 5±3° C. then washed before being re-suspended in 100 ml of AS-3 preservation solution (Caridian BCT). The end products were stored at between 2 and 8° C. The stability of the product was determined by measuring extracellular haemoglobin on the day of manufacture (D0), then 24 h later (D1), 48 h later (D2), etc. This measurement was performed using visible spectrophotometry at 577 nm. The results are given below:

| Incubation time and temperature | Incubation solution | Batch No | D 0 | D 1 | D 2 | D 3 | D 7 |
|---|---|---|---|---|---|---|---|
| 24 h/ 5 ± 3° C. | SAG-Mannitol | ERY-ASP-121211-CG-01 | 0.107 | 0.118 | 0.187 | — | 0.186 |
| | SAG-Mannitol | ERY-ASP-121218-CG | 0.06 | 0.073 | 0.088 | — | — |
| | AS-3 | ERY-ASP-121218-MA | 0.104 | 0.128 | 0.140 | — | — |

Incubation of the RBCs in AS-3 or SAG-Mannitol led to similar results. The products exhibit very good stability for at least 48 h with extracellular haemoglobin levels lower than 0.2 g/dl, and similar results can be expected at D7 as shown for the batch ERY-ASP-121211-CG-01.

EXAMPLE 4

Improvement in Cell Yield

The claimed method as illustrated in Example 1 leads to improved stability of the product. However, this has a negative impact on the cell yield of the method (~55% versus ~65% for the method described in EP 1 773 452). To obtain a better cell yield whilst maintaining good stability of the product, one of the washing parameters was modified for the 2 cycles of the claimed method. In short, the batches were produced under the conditions of Example 1 with the exception of the outflow rate of the supernatant set at 100 ml/min instead of 350 ml/min, during centrifugations of the cell suspensions. This allowed the RBC detector to perform quicker detection of the limit between the supernatant and RBCs. The quantity of RBCs sent to the waste pouch was reduced and the cell yield of the method was increased. The mean yield for the method described in Example 4 is 73% versus 54% for the method in Example 1. The stability of the product is substantially the same.

Measurement of extracellular haemoglobin (g/dl) by Excell 2280 spectrophotometry and cell yield in % A):

| | D0 | D1 | D2 | D3 | Cell yield |
|---|---|---|---|---|---|
| Method in EP1773452 | 0.3 ± 0.08 | 0.83 ± 0.22 | 1 ± 0.22 | 1.08 ± 0.22 | ~65% (mean of 189 batches) |
| Method in Example 1 | 0.11 ± 0.02 | 0.11 ± 0.03 | 0.12 ± 0.03 | 0.13 ± 0.03 | ~54 ± 3% (mean of 5 batches) |
| Method in Example 4 | 0.08 ± 0.02 | 0.13 ± 0.04 | 0.13 ± 0.06 | 0.15 ± 0.06 | ~73 ± 5% (mean of 9 batches) |

EXAMPLE 5

Reduction in Extracellular Haemoglobin Level after Optimisation of the Production Method The single FIGURE compares the extracellular haemoglobin levels found in products produced according to the method described in patent EP 1 773 452 with those of the method in Example 1. The reduction in extracellular haemoglobin after a storage time of 72 h is significant since it drops from 1.5 g/dl for the method in EP 1 773 452 to a value below 0.2 g/dl after optimisation, i.e. a reduction in haemoglobin level of more than 7.

The invention claimed is:

1. A method for obtaining a stabilised suspension of red blood cells (RBCs) encapsulating an active ingredient, from completely resealed RBCs incorporating the active ingredient, the method comprising the incubation of the resealed RBCs in an incubation solution, at an osmolality of no less than 280 mOsmol/kg, for a time of 30 minutes or more, or a time of 30 minutes to about 3 hours, the incubation solution being a solution that does not contain an agent which is denaturing for the RBC membrane, the liquid medium is then removed from the incubated suspension and the RBCs obtained are placed in suspension in a solution allowing the injection of the suspension in a patient;
   wherein the incubation solution does not contain a bridging or cross-linking agent; and
   wherein the resealed RBCs were not treated with, nor do they contain, a bridging or cross-linking agent.

2. The method of claim 1, comprising, before incubation, encapsulating by lysis-resealing the active ingredient into RBCs and obtaining resealed RBCs comprising the active ingredient.

3. The method according to claim 1, wherein the incubation is performed at an osmolality of between 280 and about 380 mOsmol/kg.

4. The method according to claim 1, wherein the incubation is performed at an osmolality of between about 290 and about 330 mOsmol/kg.

5. The method of claim 1, wherein the incubation has a duration that is 1 h or longer.

6. The method of claim 1, further comprising washing the resealed RBCs before the incubation.

7. The method of claim 6, wherein washing comprises at least one washing cycle comprising dilution of or placing in suspension the resealed RBCs in a solution, at an osmolality of no less than 280 mOsmol/kg, then separation.

8. The method of claim 7, wherein washing comprises 2 or 3 washing cycles.

9. The method according to claim 1, comprising:
(a) providing the resealed RBCs incorporating the active ingredient;
(b) obtaining a suspension or residue comprising the RBCs incorporating the active ingredient and a solution at an osmolality of 280 mOsmol/kg or higher;
(c) incubating the residue or suspension of step (b) as such or after addition of an incubation solution at an osmolality of 280 mOsmol/kg or higher, for a time of 30 minutes or longer;
(d) eliminating the liquid medium from the suspension incubated at step (b),
(e) placing in suspension the RBCs obtained at (d) in a solution allowing injection of the suspension in a patient, preferably a preservation solution allowing injection of the suspension in a patient.

10. The method according to claim 9, wherein step (b) comprises at least one 1 washing cycle, by dilution of the suspension or residue obtained at (a) in a solution, at an osmolality of 280 mOsmol/kg or higher, then obtaining a residue or suspension of RBCs.

11. The method of claim 9, wherein at step (d) either a separation is performed, or a dilution before separation.

12. The method of claim 1, wherein the incubation step is conducted at a temperature of between about 2 and about 39° C.

13. The method of claim 1, wherein:
the incubation step is conducted at low temperature between about 2 and about 10° C., and lasts about 1 h to about 72 h; or
the incubation step is conducted at a temperature between about 20 and about 39° C., and lasts about 30 min to about 1 h.

14. The method according to claim 1, comprising the recovering of a stabilised RBC suspension having an extracellular haemoglobin level maintained at 0.5 or lower and/or a haemolysis rate maintained at 2 or less at 72 h after placing in suspension in the preservation solution and at a temperature of between 2 and 8° C.

15. The method according to claim 1, comprising the recovering of a stabilised RBC suspension having an extracellular haemoglobin level maintained at 0.5 or lower and/or a haemolysis rate maintained at 2 or less for a time of between 24 h and 20 days after placing in suspension in the preservation solution and at a temperature of between 2 and 8° C.

16. The method according to claim 1, wherein the active ingredient is selected from the group consisting of L-asparaginase, IHP, ADI, Factor VIII, Factor IX, alglucosidase, beta-glucosidase, bisphosphonates, particularly $2^{nd}$ and $3^{rd}$ generation, uricase, thymidine phosphorylase, and adenosine deaminase.

* * * * *